United States Patent [19]
Dimov et al.

[11] 4,329,185
[45] May 11, 1982

[54] METHOD FOR THE PREPARATION OF A BIOLOGICALLY ACTIVE POLYAMIDE NET

[75] Inventors: Kiril D. Dimov; Nikelay B. Vassilev; Dimiter G. Dimitrov; Ekaterina I. Terlemezyan; Angelina H. Georgieva; Borislav A. Dimitrov, all of Sofia, Bulgaria

[73] Assignee: DSO "Pharmachim", Sofia, Bulgaria

[21] Appl. No.: 226,757

[22] Filed: Jan. 21, 1981

[51] Int. Cl.³ .............................................. B08B 30/00
[52] U.S. Cl. ............................................ 134/26; 3/1; 128/344; 422/28
[58] Field of Search ............. 128/334 R; 3/1; 422/28; 134/26

[56] References Cited

U.S. PATENT DOCUMENTS

| | | | |
|---|---|---|---|
| 2,423,475 | 7/1947 | Bice et al. | 422/28 |
| 2,900,644 | 8/1959 | Rosenberg et al. | 128/334 R |
| 3,124,136 | 3/1964 | Usher | 128/334 R |

FOREIGN PATENT DOCUMENTS

2456174 8/1976 Fed. Rep. of Germany ........ 422/28

*Primary Examiner*—S. Leon Bashore
*Assistant Examiner*—Michael Goldman

[57] ABSTRACT

A biologically creative polyamide net which is non-allergenic, non-carcinogenic, non-toxic and compatible with the human body is obtained by treating a polyamide net knit in a sequence of washing operations and activating the net with a solution of a antibacterial composition at elevated temperatures.

2 Claims, No Drawings

METHOD FOR THE PREPARATION OF A BIOLOGICALLY ACTIVE POLYAMIDE NET

This invention relates to a biologically active polyamide net designed for implantation in the human body by means of surgical intervention, and to a method for the preparation thereof.

Heretofore, a wide variety of surgical nets have been employed for implantation in the human body. Typical of the materials employed for such purposes are polyamides, polyesters, polypropylene, polyethylene, polytetrafluoroethylene, metals and the like. Unfortunately, most of these materials have been rejected by the protective reaction of the human organism. Although certain materials, for example, carboxymethylcellulose based materials and polyvinylalcohol fibers, are resorbed by the human organism, they are not suitable for supporting or preparing barriers between the human organs. This is attributed to the fact that, following resorbtion, the area treated grows weaker than other tissue and is frequently torn.

Among the more popular of the many methods for obtaining biologically active polyamide fibers is that which involves treating polyamide fibers with an aqueous solution of a potassium salt of 5-nitric-8-oxyquinoline or 5,7 dichloro-8 oxyquinaldine at elevated temperatures for a time period of the order of 30 minutes. Although satisfactory from several standpoints, this procedure suffers from the limitations of other known procedures in that the admixture and low molecular weight compounds from the polyamide fibers are not separated. Nets so obtained, when implanted in the human body, often result in suppuration and, typically, are incompatible with living tissue.

In accordance with the present invention, these prior art limitations are effectively obviated by means of a biologically active polyamide net which is compatible with the human body, non-toxic, non-carcinogenic and which does not provoke rejection.

The first step in the practice of the present invention involves preparing a polyamide net knit. This end is effected by the use of from 3–6 fibers having a thickness ranging from 5–10 Tex, a general preference existing for fibers of 7.6 Tex thickness. The fibers chosen may have up to 5-0 twists per meter and preferably 350 twists. The cells of the resultant net have dimensions of the order of 1.0/1.5 mm (horizontally)×1.2/2.0 mm (vertically). The net so obtained is of high strength, elastic and hygroscopic.

In order to assure acceptance by the human body, the net is then treated as follows: Initially, it is washed twice with a non-ionogenic washing medium, such as alkylphenylpolyglycolether, for a time period ranging from 5–30 minutes at a temperature within the range of 20°–90° C. A general preference for washing is found to occur at 90° C. for 15 minutes. Immediately thereafter, the net is treated first with boiling water for a time period ranging from 5–30 minutes, preferably 15 minutes, and then with water having a temperature ranging from 1°–30° C., preferably 15° C. Then, the net is treated with alcohol or acetone for a time period ranging from 5–30 minutes, preferably 15 minutes, at room temperature while mixing. Following this step, two rinsings with distilled water are effected at a temperature ranging from 10°–15° C. and the net drained up to a residual humidity of 50%. Then, the net is treated at a temperature ranging from 20°–90° C. for a time period ranging from 5–120 minutes with solutions of an antibacterial preparation which is compatible with the human body and does not provoke rejection. In other words, the antibacterial preparation must be selected from among these compositions which do not cause allergies, are non-toxic and non-carcinogenic and do not adversely affect the human body. Antibacterial compositions found suitable for this purpose may be selected from among derivatives of 8-oxyquinoline, 8-oxyquinaldine, nitrofuranic derivatives, metal salts, and the like.

Finally, the net is rinsed with water at a temperature ranging from 5°–30° C. over a time period ranging from 5–30 minutes, preferably 15 minutes, and dried at 20°–100° C. up to a residual humidity ranging from 2–4%.

The resultant biologically active net so obtained contains from 0.1 to 5 percent, by weight, of antibacterial preparation, relative to the weight of the net. The preparation is connected to the polyamide net so as to ensure a prolonged action. Consequently, the net is usable without sterilization or the need for any special cover. Additionally, it may be directly applied without the danger of a septic reaction and the slow resorbtion of the net by the human body so that it will have adequate strength during the period of recreation.

Several examples of the present invention are set forth below. It will be appreciated by those skilled in the art that these examples are solely for purposes of exposition and are not to be construed as limiting.

EXAMPLE 1

100 grams of a polyamide net comprising a knit of polyamide fibers (7.6 Tex and 360 twists with cell dimensions of 1.2/13 mm) was treated twice with methylphenylpolyglycolether for 15 minutes at 90° C. Following, the net was treated with boiling water for 15 minutes and then with water at 20° C. for 15 minutes. Next, it was treated with methyl alcohol while mixing for 15 minutes at room temperature. Then, the net was rinsed twice with distilled water at 20° C. for 15 minutes and drained up to a 50% residual humidity. The drained net was then treated with an aqueous solution of a potassium salt of 5-nitric-8-oxyquinoline having a concentration of 1 gram per liter, treating being continued for 30 minutes at 70° C. Finally, the net was washed with water at 20° C. and dried at 50° C. until a 4% residual humidity was obtained. The antibacterial preparation was present in an amount of 1 percent, by weight, relative to the weight of the net. The net so obtained was subsequently inserted in the human body by surgical intervention and there was no evidence of incompatibility with the body.

EXAMPLE 2

The procedure of example 1 was repeated with the exception that an ethyl alcohol solution of 5.7-dichloro-8-oxyquinaldine having a concentration of 1 gram per liter was employed rather than the potassium salt of 5-nitro-8-oxyquinoline. The antibacterial composition had a concentration of 1 percent, by weight, relative to the weight of the net. The resultant net was inserted in the body of a test animal by surgical intervention and was found to be compatible therewith.

EXAMPLE 3

The procedure of example 1 was repeated with the exception that an ethyl alcohol solution of 5-nitro-8- oxyquinoline having a concentration of 1 gram per liter was substituted for the potassium salt. The resultant antibacterial polyamide net was inserted in the body of a test animal and found to be compatible therewith.

EXAMPLE 4

The procedure of example 1 was repeated with the exception that an ethyl alcohol solution of N-(5-nitro-2-furfurilidene-p-phenetidine) having a concentration of 2 gram per liter was employed rather than the potassium salt. The antibacterial preparation had a concentration of 2 percent, by weight, relative to the weight of the polyamide net. The antibacterial polyamide net was inserted in the body of a test animal by surgical intervention and found to be compatible therewith.

EXAMPLE 5

The procedure described in example 1 was repeated with the exception that a dimethylformamide solution of N-(5-nitro-2-furfurilidene-3-amine-2 oxazolidone) having a concentration of 1 gram per liter was employed rather than the potassium salt. Following the antibacterial preparation of the net, the net was subjected to extraction using diethyl ether. The antibacterial preparation had a concentration of 1 percent, by weight, relative to the weight of the net. The polyamide net so prepared was inserted in the body of a test animal and was found to be compatible therewith.

EXAMPLE 6

The procedure of example 1 was repeated with the exception that an ethyl alcohol solution of N-(5-nitro-2-furfurilidene-1 aminohydantoin) having a concentration of 1 gram per liter was employed rather than the potassium salt. The antibacterial preparation had a concentration of 1 percent, by weight, relative to the weight of the net. The antibacterial polyamide net was inserted in the body of a test animal and found to be compatible therewith.

EXAMPLE 7

The procedure of example 1 was repeated with the exception that a water ethyl alcohol solution of N-cetyl-pyridine bromide having a concentration of 5 grams per liter was substituted for the potassium salt. The solvent employed had a water:alcohol ratio of 60:40. The antibacterial preparation had a concentration of 5 percent, by weight, relative to the weight of the polyamide net. The antibacterial polyamide net was inserted in the body of a test animal and was found to be compatible therewith.

EXAMPLE 8

The procedure of example 1 was repeated with the exception that the net, not being dried, was treated with an aqueous solution of silver nitrate having a concentration of 2 grams per liter. The potassium salt of 5-nitro-8-oxyquinoline contained in the net had a concentration of 1 percent, by weight, relative to the weight of the net. The silver in the net had a concentration of 1.2 percent by weight relative to the weight of the net. The antibacterial polyamide net was so obtained and inserted into a human body by surgical intervention and subsequent studies revealed that it was compatible therewith.

EXAMPLE 9

This example described the clinical administration of the antibacterial polyamide net of the invention as set forth in example 1.

In the General Surgical Department of the Higher Military General Institute, 16 patients (9 women and 7 men) were surgically treated with antibacterial net, obtained by the conditions of example 1, over a period of about one year. The majority of those treated were in the 50–60 year-old age range and most of the patients had disturbed fatty metabolism as well as cardiovascular and respiratory diseases. The defect size in those treated ranged from 62–450 cc. It was noted that defects appeared in seven patients after medium inferior laparotomy, in three patients after Fyodorov laparotomy in the right hypochondrium, and in the remaining patients after herniotomies in connection with inguinal hernias. Efforts were made in all cases to close the defects by means of autoplastics (typically from 1–5 times). However, these efforts were not satisfactory.

In the preoperative period, special attention was given to the preparation of the cardiovascular and respiratory systems which were adopted to function in the unusual conditions connected with the shift of part of the abdominal organs in the eventration. The effect of these preparative procedures was controlled by means of Stange's Test, the orthostatic test, the ECG, the pulse character, the breathing frequency, and the blood pressure values.

The type, character and amount of the surgical intervention was determined by the local tissue alterations, the patient's general status and the results of the aforementioned preoperative preparations of the cardiovascular and respiratory systems.

The skin cicatrix was cut by means of an oval skin incision. Then, the hernial sac was separated and opened, any ingrowths being carefully removed. Next, it was cut to the end of the defect and the integrity of the peritoneum restored by means of polyamide fibers of the type described herein in net form.

In medium size defects, immediate and direct contact of the homogenous tissues was established by edge fixing without creating any tension by means of the polyamide fibers. The allotransplant, whose dimensions were larger than those of the defect, were fixed on the dried and alcohol alkalized aponeurosis by means of BTL administered in checkered form as drops. Then, two perforated tubular nylon drains were fixed on the polyamide antibacterial net for active aspiration.

In the case of larger defects, the antibacterial polyamide net was fixed immediately over the peritoneum and fixed to the edges. In the event of significant tension, the experimentally approbated model of two cloths fixed for the ventral and dorsal edge surfaces, respectively, were employed.

In the plastic restoration of the inferior parts of abdominal wall, the allotransplant is fitted under the aponeurosis and is firmly fixed to its intact parts. Any inferior free ends are not cut but then sutured over the underlying implant. The operative procedure was concluded by the fitting of tubular nylon drains.

In the first postoperative day, a sandbag was placed over the bandage, a tightening dressing applied by means of a bed sheet, thereby aiding the even suppression of the subcutaneous fatty tissue to the underlying tissues. This greatly reduces any likelihood of accumulating serous liquor and permits active moves in bed.

The nylon drains were removed on the fourth or fifth day following surgical intervention.

Early complications such as suppuration, dehiscence, APP, elimination, etc., were not observed in any of these patients. All patients were evaluated every 3 months and the longest period of observation for a patient was one year. All were found to be active and able to work and no recurrences have been observed.

EXAMPLE 10

The same as in example 9, but it used the antibacterial polyamide net obtained under the conditions of example 8.

EXAMPLE 11

Thirty-three dogs of no specific breed of both sexes, weighing for 10-16 kg., were divided into two series. After morphine premedication (1 sgr/kg weight) and introductory narcosis of thiopental (20 mlgr/kg weight), the test animals were intubated and the narcosis maintained with ether and oxygen.

Series I—(16 test animals)—

A skin section, typical for middle and upper laparotomy was made. Then, a defect of the anterior abdominal wall was made, 5-10 cm in size, by cutting the aponeurosis and muscles to the peritoneum. Thorough hemostasis was then made without blood vessel ligation. The homogenous tissues of the anterior abdominal wall were then brought in direct contact and fixed with polyamide threads of the example 2 of the invention. The aponeurosis above and around the suture was dried and alkalized by 76° alcohol. Then antimicrobic polyamide cloth, 12 cm in length and 6 cm in width, was fitted on it. BTL drops were then applied in checkered fashion, the drops passing through the cells and reaching the aponeurosis and polymerizing in 50-60 seconds, thereby fixing the transplant to the lining tissue in a safe and reliable manner. A tubular nylon drain for active aspiration was then fitted after the formation of the polymer layer over the polyamide cloth.

Series II—(17 test animals)—

A defect of the anterior abdominal wall was made as described in Series I, but the peritoneum was also removed apart from the aponeurosis and the muscles.

Two pieces of antibacterial polyamide cloth prepared in accordance with the invention were cut, 11 cm in length by 6 cm in width. One piece was placed directly on the intestinal folds and the other on the aponeurosis. The allotransplant was then stitched to the edges of the matrix sutures, polyamide thread being used for stitching. The surgery was completed by fixing a fenestration tubular nylon drain.

All test animals experienced a smooth and calm postoperative period. The surgical wounds healed primarily and no splitting or suppuration was observed. On predetermined days—3d, 11th, 21st, 30th and 90th—following surgery, the dogs were again operated upon.

Examination (on the 3d day after surgery) revealed poorly expressed edema in the tissues and the collection of a scanty amount of liquor of yellowish color in the subcutaneous areas. Fibrin was deposited on the surgical net which filled the cells and was easily separated on touching. The adhesive substance was fragmented and serofibrous exudate was discovered near the fragments as well as scanty lymphocytic infiltrate. It was noted that some of the blood vessels were very full with blood. Granulation tissue and a large quantity of newly formed vessels were observed in the transplant periphery sections.

By the 11th day, the adhesive not not yet been resorbed, not withstanding the fact that it was split into fine small fragments. Young granulation tissue, lymphocytic infiltrates and developed collagenous and fibrous tissue were seen on the surfaces in contact with the adhesive substance. The surgical polyamide net was found to be covered with a fibrinlike mass which could not be easily separated.

An ample amount of reticular fibers and collagen were seen on the 21st day after the operation. In those areas where the adhesive was applied in larger quantities, there were gigantic cells forming a granuloma of "foreign body" type localized among the fibrous tissues. The polyamide cloth was strongly bound to the edges of the wound defect and was covered by granular tissue.

On the 30th day, the reticular fiber net in the area of the wound was thicker. The granulation torus on the polyamide cloth was thicker than 3-4 mm in the center and was also thicker in the periphery.

By the 90th day, shining inclusions, most probably allotransplant particles, were seen in the giant cell protoplasm.

During the reoperation, the antibacterial polyamide cloth in 7 of the test animals was found ingrown with intestinal folds and the large omentum. The granulation tissue allotransplant ingrowth in those cases commenced not only on the side of the anterior abdominal wall muscles but also by the serous membrane of the accretion of the abdominal organs.

EXAMPLE 12

The same as in Example 11, but it used the antibacterial polyamide net prepared under conditions of Example 3.

EXAMPLE 13

The same as in Example 12, but it used the antibacterial polyamide net prepared under conditions of Example 4.

EXAMPLE 14

The same as in Example 11, but with the use of antibacterial polyamide net prepared under conditions of Example 5.

EXAMPLE 15

The same as in the Example 11, but with the use of antibacterial polyamide net prepared under conditions of Example 6.

EXAMPLE 16

The same as in Example 11, but with the use of antibacterial polyamide net prepared under conditions of Example 7.

Although the invention is illustrated and described with reference to a plurality of embodiments thereof, it is to be expressly understood that it is in no way limited to the disclosure of such preferred embodiments but is capable of numerous modifications within the scope of the appended claims.

We claim:

1. Method for the preparation of a biologically active polyamide net for insertion in the human body by means of a surgical intervention which comprises sequentially treating a knit of polyamide fibers of 5-10 Tex thickness and up to 500 twists per meter with cell dimensions of the order of 1.0/1.5×1.2/2.0 mm by:
- (a) washing said net with a nonionogenic medium at a temperature of from 20°–90° C. for a time period of from 5–30 minutes;
- (b) treating the net with boiling water for a time period ranging from 5–30 minutes;
- (c) treating the net with water at a temperature of 1°–30° C.;
- (d) treating the net with a solvent selected from the group consisting of acetone and an organic alcohol for a time period of from 5–30 minutes at room temperature while mixing the solvent;
- (e) washing the net with distilled water and draining it up to 50 percent residual humidity;
- (f) treating the net at a temperature within the range of 20°–90° C. for a time period ranging from 5–120 minutes with a non-allergenic, non-toxic and non-carcinogenic antibacterial composition selected from the group consisting of:
  - (1) derivatives of 8-oxyquinoline;
  - (2) derivatives of 8-oxyquinaldine;
  - (3) nitrofuranic derivatives; and
  - (4) metal salts of derivatives of 8-oxyquinolines, derivatives of 8-oxyquinaldines, or nitrofuranic derivatives.
- (g) washing the net with water at 5°–30° C. for a time period ranging from 5–30 minutes, and
- (h) drying the treated net at a temperature ranging from 20°–100° C. up to a residual humidity ranging from 2–5 percent.

2. Method in accordance with claim 1 wherein said antibacterial composition is a potassium salt of 5-nitro-8-oxyquinaline.

* * * * *